US011717151B2

(12) United States Patent
Shen et al.

(10) Patent No.: US 11,717,151 B2
(45) Date of Patent: Aug. 8, 2023

(54) METHOD FOR EARLY DIAGNOSIS OF KERATOCONUS BASED ON MULTI-MODAL DATA

(71) Applicants: SHANGHAI MEDIWORKS PRECISION INSTRUMENTS CO., LTD., Shanghai (CN); EYE AND ENT HOSPITAL OF FUDAN UNIVERSITY, Shanghai (CN)

(72) Inventors: Yang Shen, Shanghai (CN); Xingtao Zhou, Shanghai (CN); Huijie Li, Shanghai (CN); Chongyang Wang, Shanghai (CN); Wenguang Chen, Shanghai (CN); Jing Zhao, Shanghai (CN); Meiyan Li, Shanghai (CN); Yiyong Xian, Shanghai (CN); Haipeng Xu, Shanghai (CN); Lingling Niu, Shanghai (CN); Wuxiao Zhao, Shanghai (CN); Tian Han, Shanghai (CN)

(73) Assignees: SHANGHAI MEDIWORKS PRECISION INSTRUMENTS CO., LTD., Shanghai (CN); EYE AND ENT HOSPITAL OF FUDAN UNIVERSITY, Shanghai (CN)

(*) Notice: Subject to any disclaimer, the term of this patent is extended or adjusted under 35 U.S.C. 154(b) by 0 days.

(21) Appl. No.: 17/797,114

(22) PCT Filed: Aug. 5, 2021

(86) PCT No.: PCT/CN2021/110812
§ 371 (c)(1),
(2) Date: Aug. 3, 2022

(87) PCT Pub. No.: WO2023/272876
PCT Pub. Date: Jan. 5, 2023

(65) Prior Publication Data
US 2023/0190089 A1 Jun. 22, 2023

(30) Foreign Application Priority Data
Jun. 28, 2021 (CN) ......................... 202110717940.2

(51) Int. Cl.
*A61B 3/00* (2006.01)
*A61B 3/107* (2006.01)

(52) U.S. Cl.
CPC ............ *A61B 3/0025* (2013.01); *A61B 3/107* (2013.01); *G06T 2207/10101* (2013.01)

(58) Field of Classification Search
CPC .................. A61B 3/0025; A61B 3/107; G06T 2207/10101
See application file for complete search history.

(56) References Cited

U.S. PATENT DOCUMENTS

2017/0357879 A1 12/2017 Odaibo et al.
2020/0146812 A1* 5/2020 Klopotek ............ A61F 9/00836

FOREIGN PATENT DOCUMENTS

CN 109256207 A 1/2019
CN 110517219 A 11/2019
(Continued)

*Primary Examiner* — George Manuel
(74) *Attorney, Agent, or Firm* — Bayramoglu Law Offices LLC

(57) ABSTRACT

A method for early diagnosis of keratoconus based on multi-modal data considers a mutual relationship between both eyes using four refractive maps for corneas of the both eyes and absolute corneal elevation data, and combines the deep convolutional network method, the traditional support vector machine (SVM) method in machine learning, and the elevation map enhancement method with adjustable best-fit-sphere (BFS) to identify sensitivity and specificity of a focus and balance the sensitivity and specificity. With multi-dimensional comprehensive judgment of a keratoconus morbidity with a patient as a unit, combined with binocular data including both manual selection features and deep network
(Continued)

learning from big data, the diagnosis method has higher robustness and accuracy.

5 Claims, 4 Drawing Sheets

(56) References Cited

FOREIGN PATENT DOCUMENTS

| | | | |
|---|---|---|---|
| CN | 110717884 | A | 1/2020 |
| CN | 111160431 | A | 5/2020 |

* cited by examiner

| layer name | output size | 50-layer |
|---|---|---|
| conv1 | 112×112 | 7×7, 64, stride 2 |
| conv2_x | 56×56 | 3×3 max pool, stride 2<br>$\begin{bmatrix} 1\times1, 64 \\ 3\times3, 64 \\ 1\times1, 256 \end{bmatrix} \times 3$ |
| conv3_x | 28×28 | $\begin{bmatrix} 1\times1, 128 \\ 3\times3, 128 \\ 1\times1, 512 \end{bmatrix} \times 4$ |
| conv4_x | 14×14 | $\begin{bmatrix} 1\times1, 256 \\ 3\times3, 256 \\ 1\times1, 1024 \end{bmatrix} \times 6$ |
| conv5_x | 7×7 | $\begin{bmatrix} 1\times1, 512 \\ 3\times3, 512 \\ 1\times1, 2048 \end{bmatrix} \times 3$ |
| output | 1×2 | mean pool, FC, Softmax |

FIG. 4

METHOD FOR EARLY DIAGNOSIS OF KERATOCONUS BASED ON MULTI-MODAL DATA

CROSS REFERENCE TO THE RELATED APPLICATIONS

This application is the national phase entry of International Application No. PCT/CN2021/110812, filed on Aug. 5, 2021, which is based upon and claims priority to Chinese Patent Application No. 202110717940.2, filed on Jun. 28, 2021, the entire contents of which are incorporated herein by reference.

TECHNICAL FIELD

The present disclosure relates to an ophthalmic data diagnosis technology, and in particular, to a method for early diagnosis of keratoconus based on multi-modal data.

BACKGROUND

Keratoconus is a clinical ophthalmic disease characterized by corneal dilation, central thinning, forward protrusion, and conical shape. Such disease is a contraindication to refractive surgery, occurs in one or both eyes, and usually results in a significant loss of vision. The keratoconus usually develops first from the posterior corneal surface, and then gradually develops to the anterior corneal surface.

At present, diagnosis and treatment of the keratoconus has developed into a clinical disease with close cooperation of keratopathy, refractive surgery, and optometry. Usually, a method for diagnosing the keratoconus based on corneal topography is a clinical statistical method. Most of the morphological features of the corneal topography combined with clinical parameters and medical history are used to diagnose and clinically stage the keratoconus. The result of a statistical model is a summary parameter, and a parameter boundary is obtained according to a known diagnostic result data set, such as the widely used KISA index, inferior-superior (IS) index, and surface regularity index (SRI) \surface asymmetry index (SAI). Most of these methods are limited by platform data, overly rely on a limited number of artificially identified monocular features, ignore the relationship between both eyes, and fail to give a good judgment on early keratoconus and forme fruste keratoconus due to different sensitivity and specificity of different indexes.

SUMMARY

Aiming at the problem of early diagnosis of keratoconus, a method for early diagnosis of keratoconus (including subclinical asymptomatic keratoconus and forme fruste keratoconus) based on multi-modal data is provided. Based on multi-modal refractive topographic matrix data, in combination with the neural network convolution method, the eigenvalue support vector machine (SVM) method, the binocular contrast method, and the enhanced topography method with adjustable best-fit-sphere (BFS), comprehensive diagnosis results of the keratoconus are given, and the method has more excellent robustness and accuracy especially for screening and diagnosis of early posterior keratoconus and forme fruste keratoconus.

A technical solution of the present disclosure is as follows: a method for early diagnosis of keratoconus based on multi-modal data specifically includes the following steps:

1) acquiring binocular multi-modal data including four refractive maps for corneas of both eyes and absolute corneal elevation data, where the four refractive maps for the corneas include an axial curvature map of an anterior corneal surface, a relative elevation topography of the anterior corneal surface, a relative elevation topography of a posterior corneal surface, and a corneal thickness topography; and the absolute corneal elevation data includes absolute elevation data of the anterior and posterior corneal surfaces;

2) according to classified cases, associating the binocular multi-modal data with classification categories, and classifying the data according to requirements;

3) unifying data of topographies and the elevation data of the anterior and posterior corneal surfaces in the four refractive maps in step 2) into data matrices of a same size;

4) based on the above data, determining early keratoconus of the both eyes using four branch methods, which are respectively recorded as a branch A method, a branch B method, a branch C method, and a branch D method, where the branch A method is as follows: after data processing, sending all of the data matrices of the four refractive maps to a classification network of a deep convolutional network to identify sensitivity and specificity of the keratoconus and obtain a classification result P(A) output for a certain case;

the branch B method is as follows: calculating eigenvalues of each graphic data matrix in all of the data matrices of the four refractive maps, and sending eigenvalue data to a binary classification method using an SVM to identify the sensitivity and specificity of the keratoconus and obtain a classification result P(B) output for the certain case;

the branch C method is as follows: comparing the absolute elevation data of the anterior and posterior corneal surfaces with BFS data to obtain a critical threshold between keratoconus cases and normal cases, so as to determine a classification result P(C) output for the certain case; and the branch D method is as follows: obtaining optimal sensitivity and specificity as well as a probability P(D) of the keratoconus of the certain case using the critical threshold or using an SVM classification method by taking an average value, a maximum value, and a standard deviation of the data matrices of the four refractive maps for left and right eyes as feature quantities; and 5) weighting and accumulating final results in the branch A, B, C, and D methods to obtain a final probability of the keratoconus of the certain case.

Preferably, the branch A method may include the following specific steps:

A-1: performing data scaling: scaling all of the data matrices of the four refractive maps processed in step 3) to a size of 224×224 by linear interpolation;

A-2: performing data normalization: dividing data in step A-1 into a training set and a validation set according to a ratio of 7:3, then calculating means and standard deviations of the data matrices of the four refractive maps on the training set respectively to correspondingly obtain 4 means and 4 standard deviations, and then normalizing data matrices of four refractive maps for all cases with the means and the standard deviations;

A-3: based on classification network design of the deep convolutional network, performing binary classification on the data matrices of the four refractive maps using a Resnet50 classification network to identify a normal cornea and the keratoconus in one eye;

A-4: training a classification model: connecting the data matrices of the four refractive maps according to a channel to obtain an input of 4 channels, where data amplification may use rotation, translation, and random fuzzy preprocessing, and a loss function may use a binary cross entropy function; using training weights of MobileNetV3 on an IMAGENET dataset as initial weights, and then performing fine-tuning training; and finally selecting a training weight with a smallest difference between loss values of the training set and the validation set as a training result;

A-5: performing model index evaluation: making predictions on the validation set, and then comparing with a true value for evaluation to finally obtain the sensitivity and specificity of the branch A method in identifying the keratoconus; and A-6: outputting results: if test sensitivity and specificity of the training set in step A-5 meet requirements, recording probabilities of the keratoconus of the branch A method for the certain case as p(Al) and p(Ar) respectively; and outputting classification results: P(A)=p(Al), (p(Al)>p(Ar)), and p(Ar), (p(Al)<p(Ar)).

Preferably, the branch B method may include the following specific steps:

B-1: calculating axial curvature eigenvalues of the anterior corneal surface: calculating a maximum curvature point and position coordinates in a data matrix of an axial curvature of the anterior corneal surface, calculating an IS value of a difference between upper and lower refractive power at a position with a diameter of 6 mm, and calculating an SRI and an SAI within a diameter of 4.5 mm;

B-2: calculating relative elevation eigenvalues of the anterior corneal surface: calculating a maximum elevation and position coordinates in a data matrix of a relative elevation of the anterior corneal surface;

B-3: calculating relative elevation eigenvalues of the posterior corneal surface: calculating a maximum elevation and position coordinates in a data matrix of a relative elevation of the posterior corneal surface;

B-4: calculating corneal thickness eigenvalues: calculating a minimum thickness and position coordinates in a data matrix of a corneal thickness, and calculating a thickness at a corneal vertex;

B-5: calculating distance eigenvalues: calculating a distance from a position of the maximum elevation of the anterior corneal surface in step B-2 to a position of the maximum elevation of the posterior corneal surface in step B-3, calculating a distance from the position of the maximum elevation of the anterior corneal surface in step B-2 to a position of the minimum corneal thickness in step B-4, and calculating a distance from the position of the maximum elevation of the posterior corneal surface in step B-3 to the position of the minimum corneal thickness in step B-4;

B-6: calculating corneal volume eigenvalues: performing volume integral on the data matrix of the corneal thickness within a radius of 4.5 mm to obtain a corneal volume;

B-7: normalizing all of the eigenvalues in steps B-1 to B-6, and dividing all of the normalized case data eigenvalues into a training set and a validation set according to a ratio of 7:3;

B-8: performing feature training on feature data of the training set normalized in step B-7 by the binary classification method using the SVM, where a radial basis function (RBF) kernel may be selected in the process, and optimal c and g are obtained to train data using cross-validation and grid-search;

B-9: performing model index evaluation: making predictions on the validation set, and then comparing with a true value for evaluation to finally obtain the sensitivity and specificity of the branch B method in identifying the keratoconus; and B-10: outputting results: if test sensitivity and specificity of the training set in step B-9 meet requirements, recording probabilities of the keratoconus of the branch B method for the certain case as p(Bl) and p(Br) respectively; and outputting classification results: P(B)=p(Bl), (p(Bl)>p(Br)), and p(Br), (p(Bl)<p(Br)).

Preferably, the branch C method may include the following specific steps:

C-1: calculating standard relative elevation data of the anterior corneal surface: for the absolute elevation data of the anterior and posterior corneal surfaces, performing spherical fitting on the absolute elevation data of the anterior corneal surface within a diameter of 8 mm to obtain a BFS value, and taking an elevation difference between the data of the anterior corneal surface and the obtained BFS as the standard relative elevation data of the anterior corneal surface;

C-2: calculating feature elevation data of the anterior corneal surface: for the absolute elevation data of the anterior and posterior corneal surfaces, removing data within a radius of 2 mm of a thinnest point for spherical fitting by taking the absolute elevation data of the anterior corneal surface within a diameter of 8 mm as a benchmark to obtain a BFS value; and offsetting 5 groups of data up and down respectively by taking the current BFS as a benchmark and 0.2 mm as a stride to obtain 11 groups of different BFS values, and taking an elevation difference between the data of the anterior corneal surface and the obtained different BFS as the feature relative elevation data of the anterior corneal surface;

C-3: calculating enhanced elevation data of the anterior corneal surface: calculating a difference between the standard relative elevation data obtained in step C-1 and the 11 groups of feature relative elevation data obtained in step C-2 to obtain 11 groups of enhanced data of the anterior corneal surface;

C-4: calculating standard relative elevation data of the posterior corneal surface: for the absolute elevation data of the anterior and posterior corneal surfaces, performing spherical fitting on the absolute elevation data of the posterior corneal surface within a diameter of 8 mm to obtain a BFS value, and taking an elevation difference between the data of the posterior corneal surface and the obtained BFS as the standard relative elevation data of the posterior corneal surface;

C-5: calculating feature elevation data of the posterior corneal surface: for the absolute elevation data of the anterior and posterior corneal surfaces, removing data within a radius of 2 mm of a thinnest point for spherical fitting by taking the absolute elevation data of the posterior corneal surface within a diameter of 8 mm as a benchmark to obtain a BFS value; and offsetting 5 groups of data up and down respectively by taking the current BFS as a benchmark and 0.2 mm as a stride to obtain 11 groups of different BFS values, and taking an elevation difference between the data of the posterior corneal surface and the obtained different BFS as the feature relative elevation data of the posterior corneal surface;

C-6: calculating enhanced elevation data of the posterior corneal surface: calculating a difference between the standard relative elevation data of the posterior corneal surface obtained in step C-4 and the 11 groups of feature relative elevation data obtained in step C-5 to obtain 11 groups of enhanced data of the posterior corneal surface;

C-7: counting a critical threshold between the keratoconus cases and the normal cases in each group of data in combination with all sample data by taking a matrix of a total of 22 groups of enhanced data of the anterior and posterior corneal surfaces obtained in steps C-3 and C-6 as a feature; and C-8: recording probabilities of the keratoconus of the branch C method for the certain case as p(Cl) and p(Cr) respectively, where p(Cl) and p(Cr) may be obtained through accumulation by taking a difference between each group of enhanced data calculated from a current case and the critical threshold obtained in step C-7 as a weight ratio; and outputting classification results: P(C)=p(Cl), (p(Cl)>p(Cr)), and p(Cr), (p(Cl)<p(Cr)).

Preferably, the branch D method may include the following specific steps:

D-1: unifying data orientations: mirroring the data matrices of the four refractive maps for the right eye in a longitudinal direction, and unifying nasal and bitamporal orientations of the data matrices of the four refractive maps for the left and right eyes;

D-2: obtaining diff diagram matrices of the four refractive maps: calculating a point-to-point difference of the data matrices of the four refractive maps for the left and right eyes respectively and then taking an absolute value to obtain the diff diagram data matrices of the four refractive maps;

D-3: calculating diff data features: calculating an average value, a maximum value, and a standard deviation of all data in the diff diagram data matrices of the four refractive maps within a diameter of 6 mm respectively as feature quantities;

D-4: counting a critical threshold between the keratoconus cases and the normal cases in each group of data in combination with all sample data by taking the 12 groups of average values, maximum values, and standard deviations of diff diagrams of the four refractive maps for the corneas of the left and right eyes obtained in step D-3 as features, or normalizing features of all types of diff data for training and testing using the SVM classification method to give the optimal sensitivity and specificity; and D-5: recording a probability of the keratoconus of the branch D method for the certain case as P(D), where P(D) may be obtained through accumulation by taking a difference between an eigenvalue of each group of diff data calculated from a current case and the critical threshold obtained in step D-4 as a weight ratio.

The present disclosure has the following beneficial effects: the method for early diagnosis of keratoconus based on multi-modal data of the present disclosure considers a mutual relationship between both eyes, and combines the deep convolutional network method, the traditional SVM method in machine learning, and the elevation map enhancement method with adjustable BFS to identify sensitivity and specificity of a focus and balance the sensitivity and specificity. With multi-dimensional comprehensive judgment of a keratoconus morbidity with a patient as a unit, combined with binocular data including both manual selection features and deep network learning from big data, the diagnosis method has higher robustness and accuracy.

BRIEF DESCRIPTION OF THE DRAWINGS

FIG. 4 is a structural diagram of a classification network in the method of the present disclosure.

DETAILED DESCRIPTION OF THE EMBODIMENTS

The present disclosure will be described in detail in conjunction with the accompanying drawings and specific embodiments. The embodiments are implemented on the premise of the technical solutions of the present disclosure. The following presents detailed implementations and specific operation processes. The protection scope of the present disclosure, however, is not limited to the following embodiments.

Figure 1:
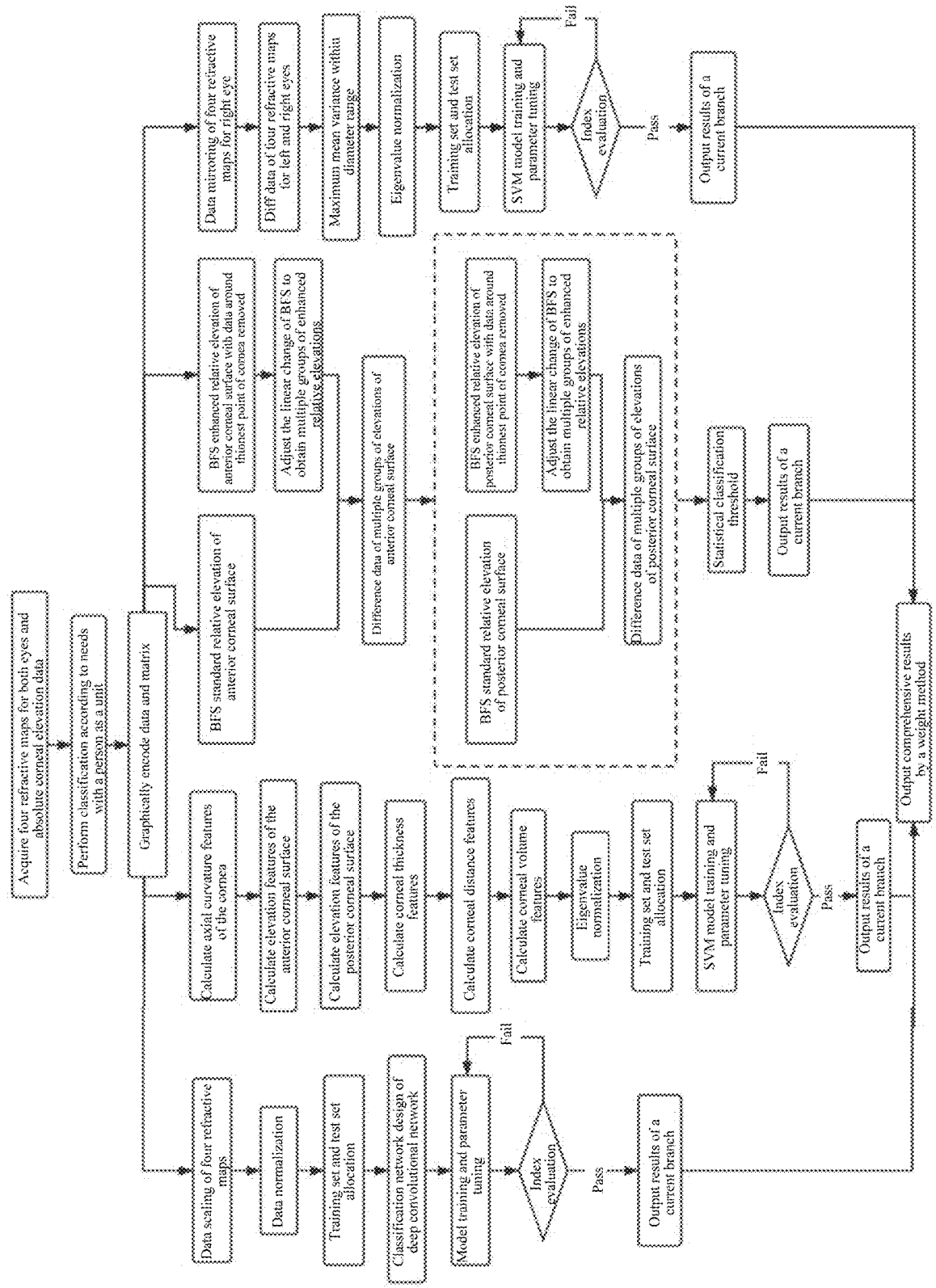
FIG. 1 is a flow chart of a method for early diagnosis of keratoconus based on multi-modal data of the present disclosure.

As shown in FIG. 1, a flow chart of a method for early diagnosis of keratoconus based on multi-modal data specifically includes the following steps.

Figure 2:
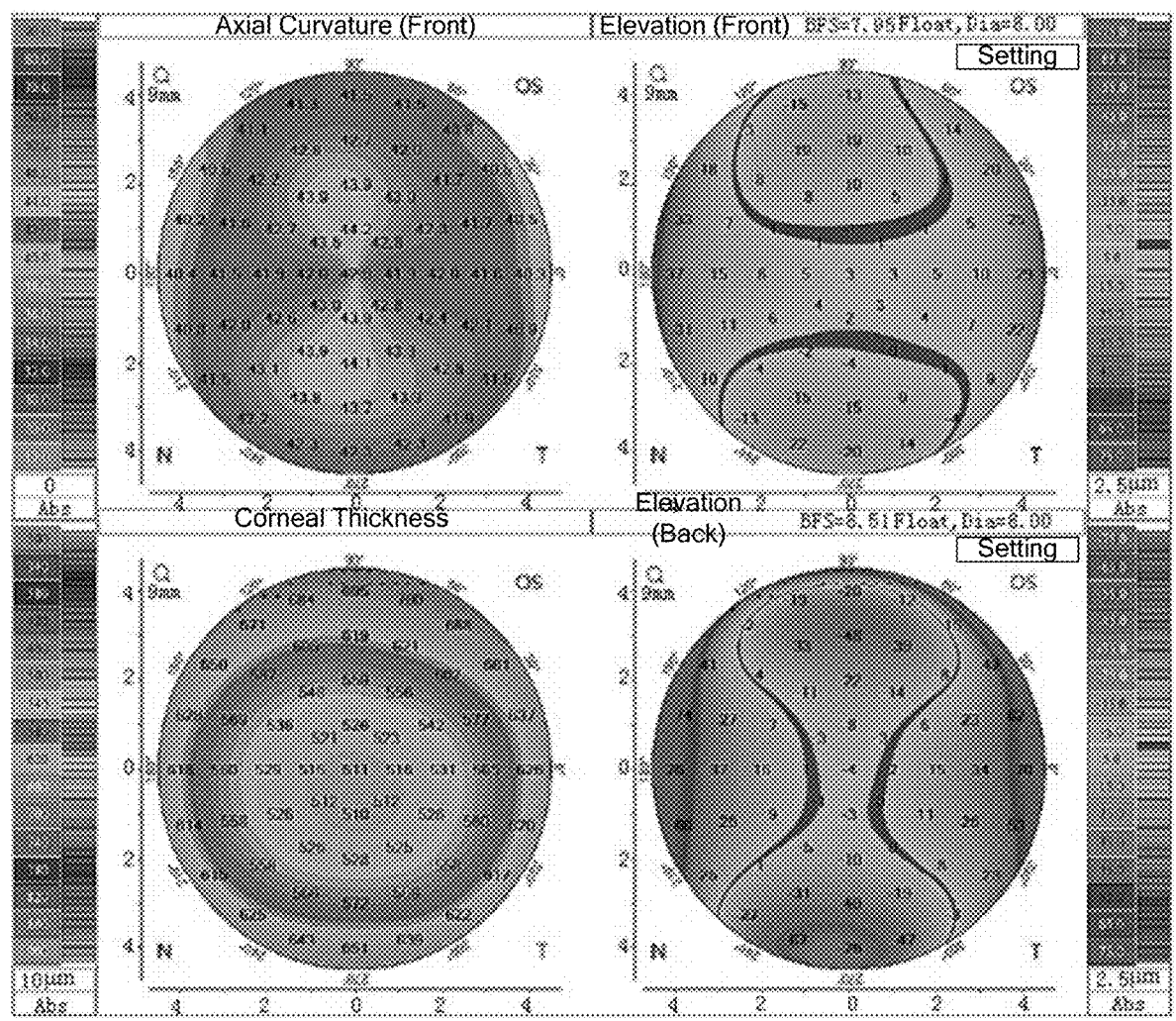
FIG. 2 shows four refractive maps for corneas.
Figure 3:
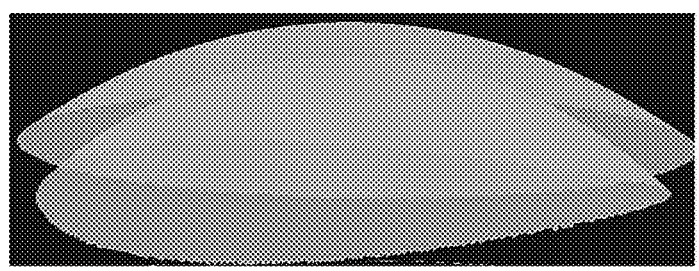
FIG. 3 shows an absolute elevation map of anterior and posterior corneal surfaces.

1. Binocular multi-modal data is acquired, including four refractive maps for corneas of both eyes and absolute corneal elevation data. The four refractive maps are obtained through a three-dimensional anterior segment analyzer or an anterior segment optical coherence tomography (OCT) measuring device. As shown in FIG. 2, the four refractive maps for the corneas include an axial curvature map of an anterior corneal surface, a relative elevation topography of the anterior corneal surface, a relative elevation topography of a posterior corneal surface, and a corneal thickness topography. FIG. 3 shows absolute elevation data of the anterior and posterior corneal surfaces.

2. According to classified cases, the binocular multi-modal data is associated with classification categories. The number of classifications depends on specific needs, such as binary classification as keratoconus and a normal cornea.

3. According to the four refractive maps for the corneas and the color corresponding code, the two-dimensional full sampling data matrix within a diameter of 9 mm of the topography is obtained with a data stride of 0.02 mm (the four maps in the four refractive maps are called topographies). The size of data of each topography and the elevation data matrices of the anterior and posterior corneal surfaces is 451×451.

4. Based on the above data, early keratoconus of the both eyes is determined using four branch methods, which are respectively recorded as a branch A method, a branch B method, a branch C method, and a branch D method.

The branch A method is as follows: this branch method takes a single case as a reference. Each data in all of the data matrices of the four refractive maps is involved in the calculation. All the factors that may affect the keratoconus judgment are retained as much as possible. The purpose of judging lesions in massive data is achieved through machine self-learning, which can be independent of the selection of human subjective features to enhance the specificity of identifying the focus.

A-1: Data scaling is performed: all of the data matrices of the four refractive maps processed in step 3 is scaled to a size of 224×224 by linear interpolation.

A-2: Data normalization is performed: data in step A-1 is divided into a training set and a validation set according to a ratio of 7:3. Then means and standard deviations of the data matrices of the four refractive maps are calculated on the training set respectively to correspondingly obtain 4 means and 4 standard deviations. Then data matrices of four refractive maps for all cases are normalized with the means and the standard deviations.

A-3: Based on classification network design of the deep convolutional network, binary classification is performed on the data matrices of the four refractive maps using a Resnet50 classification network to identify a normal cornea and the keratoconus in one eye. For the built Resnet50 classification network model, the backbone network remains unchanged, only the channel input of the first convolutional layer is modified to 4, and the output number of the finally output fully connected layer is 2. The network structure is shown in FIG. 4.

A-4: A classification model is trained: the data matrices of the four refractive maps are connected according to a channel to obtain an input of 4 channels. Data amplification uses preprocessing such as rotation, translation, and random fuzziness. A loss function uses a binary cross entropy function. Training weights of MobileNetV3 on an IMAGENET dataset are used as initial weights, and then fine-tuning training is performed. Iterative training is performed for 60 epoches with an initial learning rate of 0.01, and the learning rate is reduced by 10 times in 20 epoches and 40 epoches respectively. A training weight with a smallest difference between loss values of the training set and the validation set is finally selected as a training result.

A-5: Model index evaluation is performed: predictions are made on the validation set, and then compared with a true value for evaluation to finally obtain the sensitivity and specificity of the branch A method in identifying the keratoconus.

A-6: Results are output: if test sensitivity and specificity of the training set in step A-5 meet requirements, probabilities of the keratoconus of the branch A method for a certain case are recorded as p(Al) and p(Ar) respectively. Classification results are output: P(A)=p(Al), (p(Al)>p(Ar)), and p(Ar), (p(Al)<p(Ar)).

The branch B method is as follows: this branch method takes a single case as a reference. The features that can directly reflect the lesion are manually defined. Then the supervised learning method SVM is applied to classify whether the lesion occurs or not. The efficiency and sensitivity even under small sample data is guaranteed.

B-1: Axial curvature eigenvalues of the anterior corneal surface are calculated: a maximum curvature point and position coordinates in a data matrix of an axial curvature of the anterior corneal surface are calculated. An IS value of a difference between upper and lower refractive power at a position with a diameter of 6 mm is calculated. An SRI and an SAI within a diameter of 4.5 mm are calculated.

B-2: Relative elevation eigenvalues of the anterior corneal surface are calculated: a maximum elevation and position coordinates in a data matrix of a relative elevation of the anterior corneal surface are calculated.

B-3: Relative elevation eigenvalues of the posterior corneal surface are calculated: a maximum elevation and position coordinates in a data matrix of a relative elevation of the posterior corneal surface are calculated.

B-4: Corneal thickness eigenvalues are calculated: a minimum thickness and position coordinates in a data matrix of a corneal thickness are calculated, and a thickness at a corneal vertex is calculated.

B-5: Distance eigenvalues are calculated: a distance from a position of the maximum elevation of the anterior corneal surface in step B-2 to a position of the maximum elevation of the posterior corneal surface in step B-3 is calculated. A distance from the position of the maximum elevation of the anterior corneal surface in step B-2 to a position of the minimum corneal thickness in step B-4 is calculated. A distance from the position of the maximum elevation of the posterior corneal surface in step B-3 to the position of the minimum corneal thickness in step B-4 is calculated.

B-6: Corneal volume eigenvalues are calculated: volume integral is performed on the data matrix of the corneal thickness within a radius of 4.5 mm to obtain a corneal volume.

B-7: All of the eigenvalues in steps B-1 to B-6 are normalized, and all of the normalized case data eigenvalues are divided into a training set and a validation set according to a ratio of 7:3.

B-8: SVM is used for support vector model training. Feature training is performed on feature data of the training set normalized in step B-7 by the binary classification method using the SVM. A RBF kernel is selected in the process, and optimal c and g are obtained to train data using cross-validation and grid-search.

B-9: Model index evaluation is performed: predictions are made on the validation set, and then compared with a true value for evaluation to finally obtain the sensitivity and specificity of the branch B method in identifying the keratoconus.

B-10: Results are output: if test sensitivity and specificity of the training set in step B-9 meet requirements, probabilities of the keratoconus of the branch B method for the certain case are recorded as p(Bl) and p(Br) respectively. Classification results are output: P(B)=p(Bl), (p(Bl)>p(Br)). p(Br), (p(Bl)<p(Br)).

The branch C method is as follows: this branch method takes a single case as a reference and upgrades the traditional Belin method. It not only fully reflects the lesion features of the anterior and posterior corneal surfaces through highly enhanced data, but also improves the feature dimension by changing different BFS values, so as to improve the specificity of the statistical method and reduce the false alarm rate of false positives.

C-1: Standard relative elevation data of the anterior corneal surface is calculated: for the absolute elevation data of the anterior and posterior corneal surfaces, spherical fitting is performed on the absolute elevation data of the anterior corneal surface within a diameter of 8 mm to obtain a BFS value, and an elevation difference between the data of the anterior corneal surface and the obtained BFS is taken as the standard relative elevation data of the anterior corneal surface.

C-2: Feature elevation data of the anterior corneal surface is calculated: for the absolute elevation data of the anterior and posterior corneal surfaces, data within a radius of 2 mm of a thinnest point is removed for spherical fitting by taking the absolute elevation data of the anterior corneal surface within a diameter of 8 mm as a benchmark to obtain a BFS value. 5 groups of data are offset up and down respectively by taking the current BFS as a benchmark and 0.2 mm as a stride to obtain 11 groups of different BFS values. An elevation difference between the data of the anterior corneal surface and the obtained different BFS is taken as the feature relative elevation data of the anterior corneal surface.

C-3: Enhanced elevation data of the anterior corneal surface is calculated: a difference is calculated between the standard relative elevation data obtained in step C-1 and the 11 groups of feature relative elevation data obtained in step C-2 to obtain 11 groups of enhanced data of the anterior corneal surface.

C-4: Standard relative elevation data of the posterior corneal surface is calculated: for the absolute elevation data of the anterior and posterior corneal surfaces, spherical fitting is performed on the absolute elevation data of the posterior corneal surface within a diameter of 8 mm to obtain a BFS value, and an elevation difference between the data of the posterior corneal surface and the obtained BFS is taken as the standard relative elevation data of the posterior corneal surface.

C-5: Feature elevation data of the posterior corneal surface is calculated: for the absolute elevation data of the anterior and posterior corneal surfaces, data within a radius of 2 mm of a thinnest point is removed for spherical fitting by taking the absolute elevation data of the posterior corneal surface within a diameter of 8 mm as a benchmark to obtain a BFS value. 5 groups of data are offset up and down respectively by taking the current BFS as a benchmark and 0.2 mm as a stride to obtain 11 groups of different BFS values. An elevation difference between the data of the posterior corneal surface and the obtained different BFS is taken as the feature relative elevation data of the posterior corneal surface.

C-6: Enhanced elevation data of the posterior corneal surface is calculated: a difference is calculated between the standard relative elevation data of the posterior corneal surface obtained in step C-4 and the 11 groups of feature relative elevation data obtained in step C-5 to obtain 11 groups of enhanced data of the posterior corneal surface.

C-7: A critical threshold between the keratoconus cases and the normal cases in each group of data is counted in combination with all sample data by taking a matrix of a total of 22 groups of enhanced data of the anterior and posterior corneal surfaces obtained in steps C-3 and C-6 as a feature.

C-8: Probabilities of the keratoconus of the branch C method for the certain case are recorded as p(Cl) and p(Cr) respectively. p(Cl) and p(Cr) are obtained through accumulation by taking a difference between each group of enhanced data calculated from a current case and the critical threshold obtained in step C-7 as a weight ratio. Classification results are output: P(C)=p(Cl), (p(Cl)>p(Cr)). p(Cr), (p(Cl)<p(Cr)).

The branch D method is as follows: this branch method takes binocular cases as a reference, combines data of the four refractive maps for left and right eyes, and reflects the features of the lesion itself by extracting the difference data of the topographies of both eyes, thereby improving the identification accuracy of patients with the keratoconus as individuals.

D-1: Data orientations are unified: the data matrices of the four refractive maps for the right eye are mirrored in a longitudinal direction, such that nasal and bitamporal orientations of the data matrices of the four refractive maps for the left and right eyes are unified.

Figure 5:
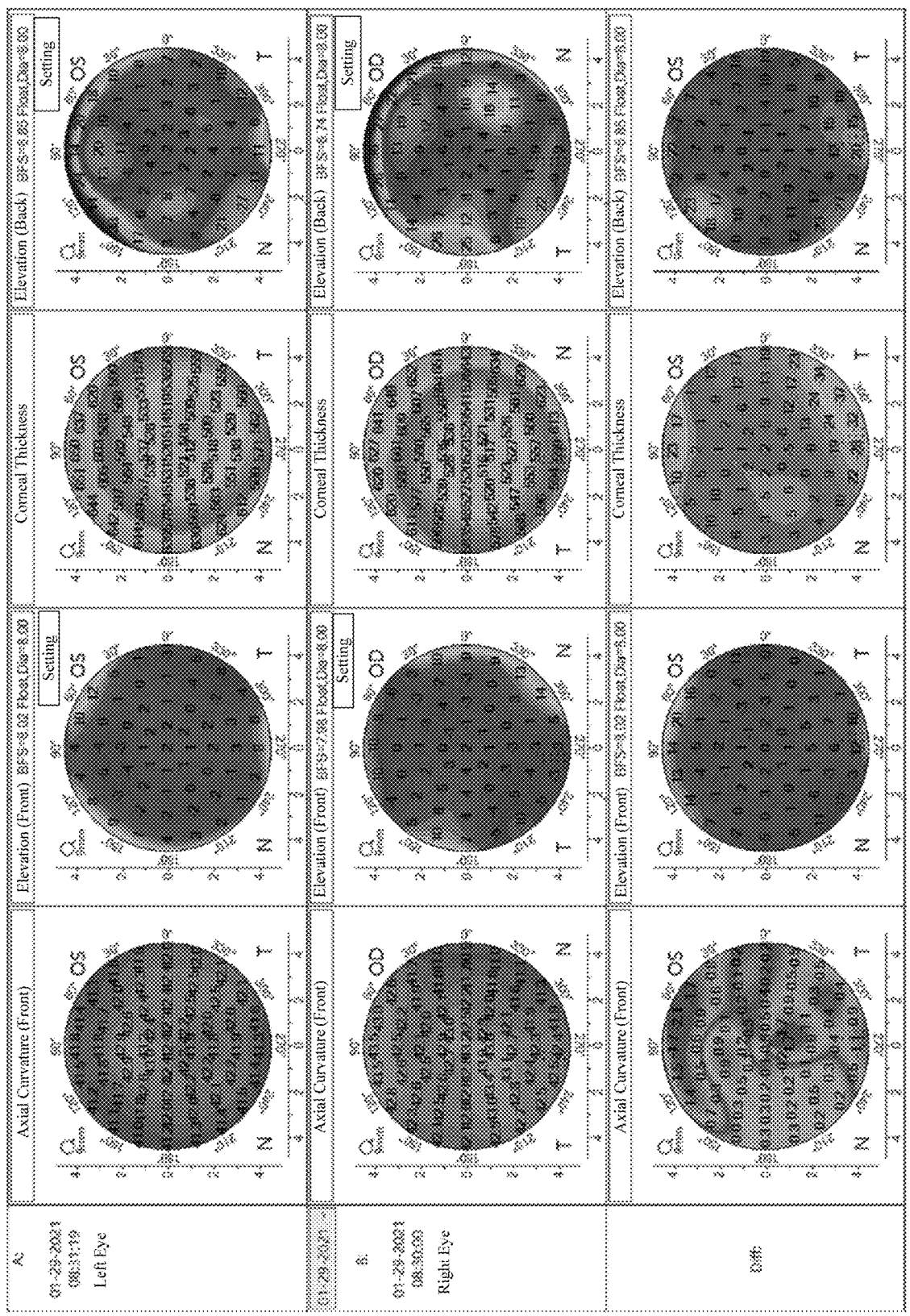
FIG. 5 shows Diff diagrams of four refractive maps for corneas of left and right eyes.

D-2: diff diagram matrices of the four refractive maps are obtained: a point-to-point difference of the data matrices of the four refractive maps for the left and right eyes is calculated respectively and then an absolute value is taken to obtain the diff diagram data matrices of the four refractive maps, as shown in FIG. 5.

D-3: diff data features are calculated: an average value, a maximum value, and a standard deviation of all data in the diff diagram data matrices of the four refractive maps within a diameter of 6 mm are calculated respectively as feature quantities.

D-4: A critical threshold between the keratoconus cases and the normal cases in each group of data is counted in combination with all sample data by taking the 12 groups of average values, maximum values, and standard deviations of diff diagrams of the four refractive maps for the corneas of the left and right eyes obtained in step D-3 as features, or features of all types of diff data are normalized for training and testing using the SVM classification method to give the optimal sensitivity and specificity.

D-5: A probability of the keratoconus of the branch D method for the certain case is recorded as P(D). P(D) is obtained through accumulation by taking a difference between an eigenvalue of each group of diff data calculated from a current case and the critical threshold obtained in step D-4 as a weight ratio.

5. Final results in the branch A, B, C, and D methods are weighted and obtained through accumulation to obtain a final probability of the keratoconus of the certain case $P=w_1*P(A)+w_2*P(B)+w_3*P(C)+w_4*P(D)/(w_1+w_2+w_3+w_4)$. $w_1$, $w_2$, $w_3$, and $w_4$ are the weights of the branch A, B, C, and D methods respectively. The acquisition of the weights should make full use of each branch method according to the target requirements, so as to achieve an optimal balance of sensitivity and specificity, and strive for the smallest false negative rate and false positive rate while ensuring robustness.

The above-mentioned embodiments only express several implementations of the present disclosure, and the descriptions thereof are relatively specific and detailed, but they should not be thereby interpreted as limiting the scope of the present disclosure. It should be noted that those of ordinary skill in the art can further make several variations and improvements without departing from the idea of the present disclosure, but such variations and improvements shall all fall within the protection scope of the present disclosure. Therefore, the protection scope of the present disclosure shall be subject to the appended claims.

What is claimed is:

1. A method for early diagnosis of keratoconus based on multi-modal data, specifically comprising the following steps:
   1) acquiring binocular multi-modal data comprising four refractive maps for corneas of both eyes and absolute corneal elevation data, wherein the four refractive maps for the corneas comprise an axial curvature map of an anterior corneal surface, a relative elevation topography of the anterior corneal surface, a relative elevation topography of a posterior corneal surface, and a corneal thickness topography; and the absolute corneal elevation data comprises absolute elevation data of the anterior and posterior corneal surfaces;
   2) according to classified cases, associating the binocular multi-modal data with classification categories, and classifying the data according to requirements;
   3) unifying data of topographies and the elevation data of the anterior and posterior corneal surfaces in the four refractive maps in step 2) into data matrices of a same size;
   4) based on the above data, determining early keratoconus of the both eyes using four branch methods, which are respectively recorded as a branch A method, a branch B method, a branch C method, and a branch D method; wherein
   the branch A method is as follows: after data processing, sending all of the data matrices of the four refractive maps to a classification network of a deep convolutional network to identify sensitivity and specificity of the keratoconus and obtain a classification result P(A) output for a certain case;
   the branch B method is as follows: calculating eigenvalues of each graphic data matrix in all of the data matrices of the four refractive maps, and sending eigenvalue data to a binary classification method using a support vector machine (SVM) to identify the sensitivity and specificity of the keratoconus and obtain a classification result P(B) output for the certain case;

the branch C method is as follows: comparing the absolute elevation data of the anterior and posterior corneal surfaces with best-fit-sphere (BFS) data to obtain a critical threshold between keratoconus cases and normal cases, so as to determine a classification result P(C) output for the certain case; and the branch D method is as follows: obtaining optimal sensitivity and specificity as well as a probability P(D) of the keratoconus of the certain case using the critical threshold or using an SVM classification method by taking an average value, a maximum value, and a standard deviation of the data matrices of the four refractive maps for left and right eyes as feature quantities; and 5) weighting and accumulating final results in the branch A method, the branch B method, the branch C method and the branch D method to obtain a final probability of the keratoconus of the certain case.

2. The method for early diagnosis of keratoconus based on multi-modal data according to claim 1, wherein the branch A method comprises the following specific steps:

A-1: performing data scaling: scaling all of the data matrices of the four refractive maps processed in step 3) to a size of 224×224 by linear interpolation;

A-2: performing data normalization: dividing data in step A-1 into a training set and a validation set according to a ratio of 7:3, then calculating means and standard deviations of the data matrices of the four refractive maps on the training set respectively to correspondingly obtain 4 means and 4 standard deviations, and then normalizing data matrices of four refractive maps for all cases with the means and the standard deviations;

A-3: based on classification network design of the deep convolutional network, performing binary classification on the data matrices of the four refractive maps using a Resnet50 classification network to identify a normal cornea and the keratoconus in one eye;

A-4: training a classification model: connecting the data matrices of the four refractive maps according to a channel to obtain an input of 4 channels, wherein data amplification uses rotation, translation, and random fuzzy preprocessing, and a loss function uses a binary cross entropy function; using training weights of MobileNetV3 on an IMAGENET dataset as initial weights, and then performing fine-tuning training; and finally selecting a training weight with a smallest difference between loss values of the training set and the validation set as a training result;

A-5: performing model index evaluation: making predictions on the validation set, and then comparing with a true value for evaluation to finally obtain the sensitivity and specificity of the branch A method in identifying the keratoconus; and A-6: outputting results: when test sensitivity and specificity of the training set in step A-5 meet requirements, recording probabilities of the keratoconus of the branch A method for the certain case as p(Al) and p(Ar) respectively; and outputting classification results: P(A) =p(Al), (p(Al)>p(Ar)), and p(Ar), (p(Al)<p(Ar)).

3. The method for early diagnosis of keratoconus based on multi-modal data according to claim 1, wherein the branch B method comprises the following specific steps:

B-1: calculating axial curvature eigenvalues of the anterior corneal surface: calculating a maximum curvature point and position coordinates in a data matrix of an axial curvature of the anterior corneal surface, calculating an inferior-superior (IS) value of a difference between upper and lower refractive power at a position with a diameter of 6 mm, and calculating a surface regularity index (SRI) and a surface asymmetry index (SM) within a diameter of 4.5 mm;

B-2: calculating relative elevation eigenvalues of the anterior corneal surface: calculating a maximum elevation and position coordinates in a data matrix of a relative elevation of the anterior corneal surface;

B-3: calculating relative elevation eigenvalues of the posterior corneal surface: calculating a maximum elevation and position coordinates in a data matrix of a relative elevation of the posterior corneal surface;

B-4: calculating corneal thickness eigenvalues: calculating a minimum thickness and position coordinates in a data matrix of a corneal thickness, and calculating a thickness at a corneal vertex;

B-5: calculating distance eigenvalues: calculating a distance from a position of the maximum elevation of the anterior corneal surface in step B-2 to a position of the maximum elevation of the posterior corneal surface in step B-3, calculating a distance from the position of the maximum elevation of the anterior corneal surface in step B-2 to a position of the minimum corneal thickness in step B-4, and calculating a distance from the position of the maximum elevation of the posterior corneal surface in step B-3 to the position of the minimum corneal thickness in step B-4;

B-6: calculating corneal volume eigenvalues: performing volume integral on the data matrix of the corneal thickness within a radius of 4.5 mm to obtain a corneal volume;

B-7: normalizing all of the eigenvalues in steps B-1 to B-6, and dividing all of the normalized case data eigenvalues into a training set and a validation set according to a ratio of 7:3;

B-8: performing feature training on feature data of the training set normalized in step B-7 by the binary classification method using the SVM, wherein a radial basis function (RBF) kernel is selected in the process, and optimal c and g are obtained to train data using cross-validation and grid-search;

B-9: performing model index evaluation: making predictions on the validation set, and then comparing with a true value for evaluation to finally obtain the sensitivity and specificity of the branch B method in identifying the keratoconus; and B-10: outputting results when test sensitivity and specificity of the training set in step B-9 meet requirements, recording probabilities of the keratoconus of the branch B method for the certain case as p(Bl) and p(Br) respectively; and outputting classification results: P(B) =p(Bl), (p(Bl)>p(Br)), and p(Br), (p(Bl)<p(Br)).

4. The method for early diagnosis of keratoconus based on multi-modal data according to claim 1, wherein the branch C method comprises the following specific steps:

C-1: calculating standard relative elevation data of the anterior corneal surface: for the absolute elevation data of the anterior and posterior corneal surfaces, performing spherical fitting on the absolute elevation data of the anterior corneal surface within a diameter of 8 mm to obtain a BFS value, and taking an elevation difference between the data of the anterior corneal surface and the obtained BFS as the standard relative elevation data of the anterior corneal surface;

C-2: calculating feature elevation data of the anterior corneal surface: for the absolute elevation data of the anterior and posterior corneal surfaces, removing data within a radius of 2 mm of a thinnest point for spherical fitting by taking the absolute elevation data of the anterior corneal surface within a diameter of 8 mm as a benchmark to obtain a BFS value; and offsetting 5 groups of data up and down respectively by taking the current BFS as a benchmark and 0.2 mm as a stride to obtain 11 groups of different BFS values, and taking an elevation difference between the data of the anterior corneal surface and the obtained different BFS as the feature relative elevation data of the anterior corneal surface;

C-3: calculating enhanced elevation data of the anterior corneal surface: calculating a difference between the standard relative elevation data obtained in step C-1 and the 11 groups of feature relative elevation data obtained in step C-2 to obtain 11 groups of enhanced data of the anterior corneal surface;

C-4: calculating standard relative elevation data of the posterior corneal surface: for the absolute elevation data of the anterior and posterior corneal surfaces, performing spherical fitting on the absolute elevation data of the posterior corneal surface within a diameter of 8 mm to obtain a BFS value, and taking an elevation difference between the data of the posterior corneal surface and the obtained BFS as the standard relative elevation data of the posterior corneal surface;

C-5: calculating feature elevation data of the posterior corneal surface: for the absolute elevation data of the anterior and posterior corneal surfaces, removing data within a radius of 2 mm of a thinnest point for spherical fitting by taking the absolute elevation data of the posterior corneal surface within a diameter of 8 mm as a benchmark to obtain a BFS value; and offsetting 5 groups of data up and down respectively by taking the current BFS as a benchmark and 0.2 mm as a stride to obtain 11 groups of different BFS values, and taking an elevation difference between the data of the posterior corneal surface and the obtained different BFS as the feature relative elevation data of the posterior corneal surface;

C-6: calculating enhanced elevation data of the posterior corneal surface: calculating a difference between the standard relative elevation data of the posterior corneal surface obtained in step C-4 and the 11 groups of feature relative elevation data obtained in step C-5 to obtain 11 groups of enhanced data of the posterior corneal surface;

C-7: counting a critical threshold between the keratoconus cases and the normal cases in each group of data in combination with all sample data by taking a matrix of a total of 22 groups of enhanced data of the anterior and posterior corneal surfaces obtained in steps C-3 and C-6 as a feature; and C-8: recording probabilities of the keratoconus of the branch C method for the certain case as p(Cl) and p(Cr) respectively, wherein p(Cl) and p(Cr) are obtained through accumulation by taking a difference between each group of enhanced data calculated from a current case and the critical threshold obtained in step C-7 as a weight ratio; and outputting classification results: P(C)=p(Cl), (p(Cl)>p(Cr)), and p(Cr), (p(Cl)<p(Cr)).

5. The method for early diagnosis of keratoconus based on multi-modal data according to claim 1, wherein the branch D method comprises the following specific steps:

D-1: unifying data orientations: mirroring the data matrices of the four refractive maps for the right eye in a longitudinal direction, and unifying nasal and bitamporal orientations of the data matrices of the four refractive maps for the left and right eyes;

D-2: obtaining diff diagram matrices of the four refractive maps: calculating a point-to-point difference of the data matrices of the four refractive maps for the left and right eyes respectively and then taking an absolute value to obtain the diff diagram data matrices of the four refractive maps;

D-3: calculating diff data features: calculating an average value, a maximum value, and a standard deviation of all data in the diff diagram data matrices of the four refractive maps within a diameter of 6 mm respectively as feature quantities;

D-4: counting a critical threshold between the keratoconus cases and the normal cases in each group of data in combination with all sample data by taking the 12 groups of average values, maximum values, and standard deviations of diff diagrams of the four refractive maps for the corneas of the left and right eyes obtained in step D-3 as features, or normalizing features of all types of diff data for training and testing using the SVM classification method to give the optimal sensitivity and specificity; and D-5: recording a probability of the keratoconus of the branch D method for the certain case as P(D), wherein P(D) is obtained through accumulation by taking a difference between an eigenvalue of each group of diff data calculated from a current case and the critical threshold obtained in step D-4 as a weight ratio.

* * * * *